United States Patent [19]

O'Murchu

[11] Patent Number: 5,210,222
[45] Date of Patent: May 11, 1993

[54] PROCESS FOR THE PRODUCTION OF MALONIC ACID ANHYDRIDE

[75] Inventor: Colm O'Murchu, Visp, Switzerland

[73] Assignee: Lonza Ltd., Gampel/Valais, Switzerland

[21] Appl. No.: 824,004

[22] Filed: Jan. 21, 1992

[30] Foreign Application Priority Data

Jan. 21, 1991 [CH] Switzerland .............................. 156/91

[51] Int. Cl.⁵ ................... C07D 305/00; C07C 67/08; C07C 69/66
[52] U.S. Cl. .................... 549/231; 560/176; 560/180; 560/204
[58] Field of Search ................ 549/231; 560/204, 176, 560/180

[56] References Cited

U.S. PATENT DOCUMENTS 4,251,447 2/1981 Perrin .................................. 260/333
4,360,691 11/1982 Perrin .................................. 560/131

OTHER PUBLICATIONS

Lapalme et al., Canadian Journal Of Chem., vol. 57, (1979), pp. 3272 to 3277.

Primary Examiner—Cecilia Tsang
Attorney, Agent, or Firm—Fisher, Christen & Sabol

[57] ABSTRACT

A process, which is harmless with respect to safety, for the production of malonic acid anhydride. For this purpose, diketene is ozonized in the presence of a suitable carbonyl compound. Malonic acid anhydride is a highly reactive intermediate product for the synthesis of numerous active ingredients for, e.g., pharmaceutical agents, pesticides or dyes.

12 Claims, No Drawings

PROCESS FOR THE PRODUCTION OF MALONIC ACID ANHYDRIDE

BACKGROUND OF THE INVENTION

1. Field Of The Invention

The invention relates to a new process for the production of malonic acid anhydride.

2. Background Art

Malonic acid anhydride is a reactive structural element for the production of numerous active ingredients for pharmaceutical agents, pesticides or dyes (see U.S. Pat. Nos. 4,251,447 and 4,360,691). Ozonizations of diketene to malonic acid anhydride are known. Perrin, in U.S. Pat. Nos. 4,251,447 and 4,360,691, claims the production of malonic acid anhydride or malonic acid anhydride derivatives by the reaction of diketene at 0° to −100° C. with ozone. But a drawback of this process, serious for safety reasons, is that insoluble formaldehyde-peroxide polymers result as a by-product in organic solvents (U.S. Pat. No. 4,360,691, column 5, lines 3 to 5), which, e.g., are highly explosive according to Lapalme et al., Can. J. Chem., Vol 57, (1979), page 3272.

BROAD DESCRIPTION OF THE INVENTION

The main object of the invention is to develop a process, which is harmless with respect to safety and is feasible on an industrial scale, for the production of malonic acid anhydride. Other objects and advantages of the invention are set out herein or are obvious herefrom to one skilled in the art.

The advantages and objects of the invention are achieved by the process of the invention.

The invention involves a process for the production of malonic acid anhydride, having the formula:

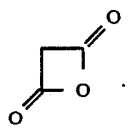   I

The process involves ozonizing diketene at a temperature between −30° and −100° C. in the presence of a carbonyl compound of formula:

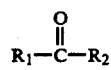   II wherein $R_1$ and $R_2$ are the same or different and are hydrogen, an alkyl group, an alkoxy group or an aryl group.

Preferably an aldehyde of formula:

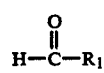   III wherein $R_1$ has said meaning, is used as the carbonyl compound. Preferably acetaldehyde is used. Preferably ozonization takes place at a temperature between −40° and −80° C. in the presence of an aprotic, anhydrous solvent.

DETAILED DESCRIPTION OF THE INVENTION

Diketene, which is available on an industrial scale, is then first ozonized at a temperature between −30° and −100° C. in the presence of a carbonyl compound of formula:

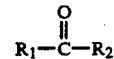   II wherein $R_1$ and $R_2$ are the same or different and are hydrogen, an alkyl group, an alkoxy group or an aryl group, to malonic acid anhydride of formula:

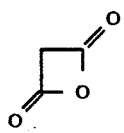   I

The ozonization in the presence of one of the carbonyl compounds results in that, instead of the formation of the formaldehyde-peroxide polymers, soluble ozonides are formed, which can be safely separated.

In the case of the radicals $R_1$ and $R_2$, alkyl suitably means a lower alkyl group with 1 to 4 C atoms, preferably a methyl, ethyl, propyl, n-butyl, isobutyl or tert-butyl group. Alkoxy suitably means a methoxy or ethoxy group. Aryl suitably means phenyl or p-toluyl, preferably phenyl.

Aldehydes of the formula:

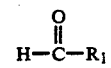   III wherein $R_1$ has said meaning, suitably are used as the carbonyl compounds. Preferred aldehydes are formaldehyde, acetaldehyde, propionaldehyde, isobutyraldehyde, pivalaldehyde, benzaldehyde or p-toluylaldehyde. Use of acetaldehyde is especially preferred.

The carbonyl compounds suitably are used stoichiometrically or in slight excess, relative to the diketene.

The reaction temperature moves between −30° and −100° C. Since the malonic acid anhydride begins to decompose at −30° C., the reaction is preferably performed at a temperature below −30° C., preferably between −40° and −80° C.

Advantageously, the reaction takes place in the presence of aprotic anhydrous solvents, such as:

in alkanes, e.g., pentane and hexane;

in aromatic hydrocarbons, e.g., $C_1$–$C_4$ alkyl-substituted benzenes, such as, toluene, ethylbenzene, dimethylbenzene, ethylmethylbenzene, propylbenzene, isopropylbenzene, butylbenzene, isobutylbenzene, diethylbenzene, mesitylene and cymene; halogenated benzenes, such as, fluorobenzene and chlorobenzene;

in ethers, e.g., dimethyl ether, diethyl ether, dipropyl ether, dibutyl ether, tertiary-butyl methyl ether, tetrahydrofuran and dioxane;

in esters, e.g., $C_1$–$C_8$ alkyl formates, such as methyl formate, ethyl formate, propyl formate, isobutyl formate, hexyl formate and octyl formate; $C_1$–$C_8$ alkyl acetates, such as methyl acetate, ethyl acetate, propyl acetate, butyl acetate, 2-ethylhexyl acetate, pentyl acetate, hexyl acetate, heptyl acetate and octyl acetate;

in nitriles, e.g., acetonitrile, propionitrile, butyronitrile, or in halogenated hydrocarbons, e.g., methylene chloride and chloroform.

It is generally advantageous to proceed so that ozone, which is generated as a gas mixture with a main portion of oxygen, is introduced in a solution of the diketene and the corresponding carbonyl compound in one of the solvents until blue coloring of the solution indicates the end of the ozonization or until the stoichiometric amount of ozone has been absorbed.

Since, as initially mentioned, the malonic acid anhydride decomposes at temperatures of $-30$ C and higher to ketene and $CO_2$, it is generally directly further processed, e.g., according to U.S. Pat. No. 4,251,447, with e.g., alcohols, phenols or amines, into the corresponding malonic acid derivatives.

EXAMPLE 1

Process for the Production of Malonic Acid Anhydride

A solution of 4.2 g (0.050 mol) of diketene and 2.2 g (0.050 mol) of acetaldehyde in 100 ml of chloroform was ozonized at $-60°$ C. with a stream of 4 percent ozone in oxygen until blue coloring of the solution occurred. The excess ozone was first flushed with oxygen, then with nitrogen. Properties of the reaction product are:

$^1$H—NMR: (reaction mixture at $-50°$ C., 300 MHz) $\delta$ in ppm:
malonic acid anhydride: 4.24, s
propylene ozonide: 1.52, d, $CH_3$, 5.1, s, CH, 5.31, q, CH, 5.32, s, CH

EXAMPLE 2

A solution of 4.2 g (0.050 mol) of diketene and 4.0 g (0.055 mol) of isobutyraldehyde in 200 ml of chloroform was ozonized at $-60°$ C. with a stream of 4 percent ozone in oxygen until blue coloring of the solution occurred. The excess ozone was flushed with nitrogen. Properties of the reaction product are:

$^1$H—NMR: (reaction mixture at $-50°$ C., 300 MHz) $\delta$ in ppm:
malonic acid anhydride; 4.24, s
3-isopropyl-1,2,4-trioxolan: 1.03, dd, $CH_3$, 2.00, m, CH, 4.93, d, CH, 5.07, s, CH, 5.31, s, CH

EXAMPLE 3

A solution of 4.2 g (0.050 mol) of diketene and 4.3 g (0.055 mol) of pivalaldehyde in 200 ml of chloroform was ozonized at $-60°$ C. with a stream of 4 percent ozone in oxygen until blue coloring of the solution occurred. The excess ozone was flushed with nitrogen. Properties of the reaction product are:

$^1$H—NMR: (reaction mixture at $-50°$ C., 300 MHz) $\delta$ in ppm:
malonic acid anhydride: 4.24, s
3-tertiary-butyl-1,2,4-trioxolan: 1.01, s, $CH_3$, 4.82, s, CH, 5.01, s, CH, 5.35, s, CH

EXAMPLE 4

A solution of 4.2 g (0.050 mol) of diketene and 5.84 g (0.055 mol) of benzaldehyde in 200 ml of chloroform was ozonized at $-60°$ C. with a stream of 4 percent of ozone in oxygen until blue coloring of the solution occurred. The excess ozone was flushed with nitrogen. Properties of the reaction product are:

$^1$H—NMR: (reaction mixture at $-50°$ C., 300 MHz) $\delta$ in ppm:
malonic acid anhydride: 4.23, s
3-tertiary-butyl-1,2,4-trioxolan: 5.41, s, CH, 5.57, s, CH, 6.07, s, CH, 7.4–7.8, m, Ph

EXAMPLE 5

A solution of 4.2 g (0.050 mol) of diketene and 6.0 g (0.055 mol) of p-toluylaldehyde in 200 ml of chloroform was ozonized at $-60$ C with a stream of 4 percent of ozone in oxygen until blue coloring of the solution occurred. The excess ozone was flushed with nitrogen. Properties of the reaction product are:

$^1$H—NMR: (reaction mixture at $-50°$ C., 300 MHz) $\delta$ in ppm:
malonic acid anhydride: 4.22, s
3-(4-methylphenyl)-1,2,4-trixolan: 2.42, s, $CH_3$, 5.39, s, CH, 5.56, s, CH, 6.03, s, CH, 7.46, d, aromatic CH

EXAMPLE 6

In the same way as indicated in Example 1, but with 100 ml of dichloromethane as the solvent, a solution of malonic acid anhydride and propylene ozonide was obtained.

EXAMPLE 7

In the same way as indicated in Example 1, but with 100 ml of toluene as the solvent, a solution of malonic acid anhydride and propylene ozonide was obtained.

What is claimed is:

1. Process for the production of malonic acid anhydride of the formula:

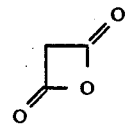

characterized in that diketene is ozonized at a temperature between $-30°$ and $-100°$ C. in the presence of a carbonyl compound of formula:

wherein $R_1$ and $R_2$ are the same or different and are hydrogen, an alkyl group having 1 to 4 carbon atoms, an alkoxy group which is methoxy or ethoxy, or an aryl group which is phenyl or p-toluyl.

2. The process according to claim 1 wherein an aldehyde of formula:

wherein $R_1$ has said meaning, is used as the carbonyl compound.

3. The process according to claim 1 or 2 wherein acetaldehyde, is used as the carbonyl compound.

4. The process according to claim 3 wherein the ozonization takes place at a temperature between $-40°$ and $-80°$ C. in the presence of an aprotic, anhydrous solvent.

5. The process according to claim 1 wherein the ozonization takes place at a temperature between $-40°$ and $-80°$ C. in the presence of an aprotic, anhydrous solvent.

6. The process according to claim 1 wherein $R_1$ and $R_2$ are alkyl groups having 1 to 4 carbon atoms.

7. The process according to claim 6 wherein $R_1$ is methyl, ethyl, propyl, n-butyl, isobutyl or ter.-butyl, and $R_2$ is methyl, ethyl, propyl, n-butyl, isobutyl or ter.-butyl.

8. The process according to claim 1 wherein $R_1$ and $R_2$ are phenyl.

9. The process according to claim 1 wherein the temperature is between $-40°$ and $-80°$ C.

10. The process according to claim 2 wherein the carbonyl compound is formaldehyde, acetaldehyde, propionaldehyde, isobutyraldehyde, pivalaldehyde, benzaldehyde or p-toluylaldehyde.

11. The process according to claim 1 wherein the carbonyl compound is used in a stoichiometically amount or in a slight excess, relative to the diketene.

12. The process according to claim 5 wherein the aprotic, anhydrous solvent is selected from the group consisting of an alkane, an aromatic hydrocarbon, an ether, a nitrile, a halogenated benzene, a $C_1$–$C_8$ alkyl formate, a $C_1$–$C_8$ alkyl acetate, methylene chlorideand chloroform.

* * * * *